United States Patent
Schwalge et al.

[11] Patent Number: 5,965,599
[45] Date of Patent: Oct. 12, 1999

[54] FUNGICIDAL MIXTURES OF AN OXIME ETHER CARBOXYLIC ACID AMIDE WITH AN N-TRICHLOROMETHYL THIOPHTALIMIDE

[75] Inventors: Barbara Schwalge, Heidelberg; Ruth Müller, Friedelsheim; Herbert Bayer; Hubert Sauter, both of Mannheim; Eberhard Ammermann, Heppenheim; Gisela Lorenz, Hambach; Siegfried Strathmann, Limburgerhof, all of Germany

[73] Assignee: BASF Atiengesellschaft, Ludwigshafen, Germany

[21] Appl. No.: 08/983,561

[22] PCT Filed: Aug. 5, 1996

[86] PCT No.: PCT/EP96/03453

§ 371 Date: Jan. 22, 1998

§ 102(e) Date: Jan. 22, 1998

[87] PCT Pub. No.: WO97/06684

PCT Pub. Date: Feb. 27, 1997

[30] Foreign Application Priority Data

Aug. 17, 1995 [DE] Germany .................. 195 30 168

[51] Int. Cl.$^6$ ............... A01N 37/18; A01N 43/38
[52] U.S. Cl. ............ 514/417; 514/421; 514/619
[58] Field of Search ................ 514/417, 421, 514/619

[56] References Cited

U.S. PATENT DOCUMENTS

| | | | |
|---|---|---|---|
| 2,553,770 | 5/1951 | Kittleson | 167/33 |
| 2,553,771 | 5/1951 | Kittleson | 260/313 |
| 5,500,441 | 3/1996 | Wingert et al. | 514/412 |

FOREIGN PATENT DOCUMENTS

95/21154  8/1995  WIPO.

Primary Examiner—Allen J. Robinson
Attorney, Agent, or Firm—Keil & Weinkauf

[57] ABSTRACT

A fungicidal mixture comprising
a) an oxime ether carboxamide of the formula I

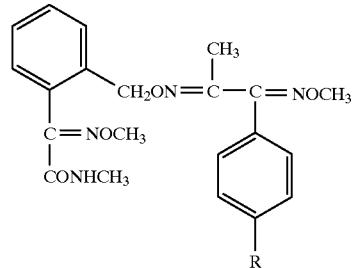

where R is hydrogen or halogen and
b) a phthalimide derivative selected from the group consisting of the compounds II and III

II

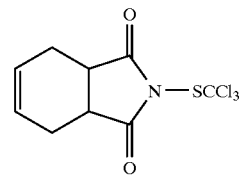

III
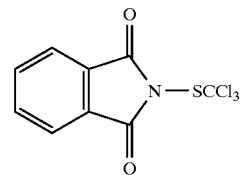

in a synergistically active amount.

8 Claims, No Drawings

FUNGICIDAL MIXTURES OF AN OXIME ETHER CARBOXYLIC ACID AMIDE WITH AN N-TRICHLOROMETHYL THIOPHTALIMIDE

This application is a 371 of PCT/EP96/03453, filed Aug. 5, 1996.

The present invention relates to a fungicidal mixture which comprises a) an oxime ether carboxamide of the formula I

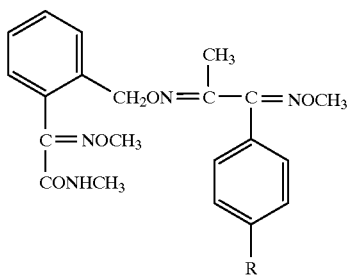

where R is hydrogen or halogen and b) a phthalimide derivative selected from the group consisting of the compounds II and III

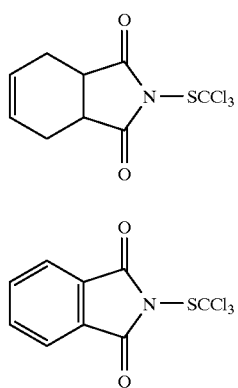

in a synergistically active amount.

Moreover, the invention relates to methods of controlling harmful fungi using mixtures of the compounds I and II or the compounds I and III and to the use of the compound I, the compound II and the compound III for the preparation of such mixtures.

The compounds of the formula I, their preparation and their action against harmful fungi are disclosed in the literature (WO-A 95/18,789). Also disclosed are the phthalimide derivatives II and III (U.S. Pat. Nos. 2,553,770; 2,553,771; 2,553,776), their preparation and their action against harmful fungi.

It was an object of the present invention to provide mixtures which have an improved action against harmful fungi combined with a reduced total amount of active ingredients applied (synergistic mixtures) with a view to reducing the rates of application and to improving the spectrum of action of the known compounds.

Accordingly, we have found that this object is achieved by the mixtures defined at the outset. Moreover, we have found that better control of the harmful fungi is possible by applying the compound I and the compound II or the compound III simultaneously together or separately or by applying the compound I and the compounds [sic] II or the compound III in succession than when the individual compounds are used.

R in formula I is hydrogen or a halogen atom such as fluorine, chlorine, bromine or iodine, especially hydrogen, fluorine and chlorine, in particular hydrogen or fluorine.

In relation to the C=N double bond, the compounds of the formula I can be present in the E or the Z configuration (in relation to the carboxylic acid function). Accordingly, they can be used in the mixture according to the invention in each case either in the form of the pure E or Z isomers or else in the form of an E/Z isomer mixture. The E/Z isomer mixture or the E isomer is preferably used, the E isomer being especially preferred.

The C=N double bonds of the oxime ether groups in the side chain of the compounds I can exist in each case in the form of pure E or Z isomers or in the form of E/Z isomer mixtures. The compounds I can be used in the mixtures according to the invention as isomer mixtures or else as the pure isomers. With a view to their use, compounds I which are particularly preferred are those where both oxime ether groups in the side chain are in the E configuration (E/E).

Due to the basic character of the NH group, the compounds I are capable of forming adducts or salts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carbonic acid, and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals such as phenyl and naphthyl which have attached to them one or two sulfo groups), alkylphosphonic acids (phosphonic acids having straight-chain or branched alkyl radicals of 1 to 20 carbon atoms), arylphosphonic acids or aryldiphosphonic acids (aromatic radicals such as phenyl and naphthyl which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can exist in the various valencies which they can assume.

When preparing the mixtures, it is preferred to employ the pure active ingredients I and II, or III, with which further active ingredients against harmful fungi or other pests such as insects, arachnids or nematodes, or else herbicidal or growth-regulating active ingredients or fertilizers can be admixed, if so required.

The mixtures of the compounds I and II, or I and III, or the simultaneous joint or separate use of the compounds I and II, or I and III, have an outstanding action against a wide spectrum of phytopathogenic fungi, in particular from the classes of the Ascomycetes and Basidiomycetes. Some of them act systemically and can therefore also be employed as foliar- and soil-acting fungicides.

They are especially important for controlling a large number of fungi in a variety of crop plants such as cotton, vegetable species (eg. cucumbers, beans and cucurbits), barley, grass, oats, coffee, maize, fruit species, rice, rye, soya, grape vine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, Puccinia species in cereals, Rhizoctonia species in cotton and lawns, Ustilago species in cereals and sugar cane, *Venturia inaequalis* (scab) in apples, Helminthosporium species in cereals, *Septoria nodorum* in wheat, *Botrytis cinera* [sic] (gray mold) in strawberries and grape vines, *Cercospora arachidicola* in groundnuts, *Pseudocercosporella herpotrichoides* in wheat and barley, *Pyricularia oryzae* in rice, *Phytophthora infestans* in potatoes and tomatoes, *Pseudoperonospora Cubense* [sic] in cucurbits, *Plasmopara viticola* in grape vines, Alternaria species in vegetables and fruit, and Fusarium and Verticillium species.

Furthermore, they can be used in the protection of materials (eg. the protection of wood), for example against *Paecilomyces variotii*.

The compounds I and II, or I and III, can be applied simultaneously together or separately or in succession, the order in the case of separate application generally not having any effect on the result of the control measures.

The compounds I and II, or I and III, are usually used in a weight ratio of 1:1 to 1:100, preferably 1:1 to 1:50, in particular 1:3 to 1:30 (I:II or III).

The application rates in the mixtures according to the invention are from 0.02 to 5 kg/ha, preferably 0.05 to 3.5 kg/ha, in particular 0.1 to 3.5 kg/ha, depending on the nature of the desired effect. In the case of the compounds I, the application rates are from 0.005 to 0.5 kg/ha, preferably 0.01 to 0.5 kg/ha, in particular 0.01 to 0.3 kg/ha. Correspondingly, the application rates in the case of the compounds II, or the compounds III, are from 0.1 to 5 kg/ha, preferably 0.1 to 3.5 kg/ha.

For seed treatment, the application rates of the mixture are generally from 0.001 to 50 g/kg of seed, preferably 0.01 to 10 g/kg, in particular 0.01 to 5 g/kg.

If it is phytopathogenic harmful fungi that are to be controlled, the separate or joint application of the compounds I and II, or I and III, or of the mixtures of the compounds I and II, or I and III, is effected by spraying or dusting the seeds, the plants or the soils before or after sowing the plants or before or after plant emergence.

The fungicidal synergistic mixtures according to the invention, or the compounds I and II, or I and III, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform a distribution as possible of the mixture according to the invention.

The formulations are prepared in a manner known per se, eg. by adding solvents and/or carriers. It is usual to admix inert additives such as emulsifiers or dispersants with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylaryl sulfonates, alkyl, lauryl ether and fatty alcohol sulfates, and salts of sulfated hexa-, hepta- and octadecanols or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol [sic] or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene [sic], lauryl alcohol polyglycol ether acetate, sorbitol esters, lignosulfite waste liquors or methylcellulose.

Powders, materials for spreading and dusts can be prepared by mixing or jointly grinding the compounds I or II, or I or III, or the mixture of the compounds I and II, or I and III, with a solid carrier.

Granules (eg. coated granules, impregnated granules or homogeneous granules) are usually prepared by binding the active ingredient, or active ingredients, to a solid carrier.

Fillers or solid carriers are, for example, mineral earths such as silica gel, silicas, silica gels [sic], silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I or II, or I or III, or of the mixture of the compounds I and II, or I and III. The active ingredients are employed in a purity of from 90% to 100%, preferably 95% to 100% (according to NMR or HPLC spectrum [sic]).

The compounds I or II, or I or III, or the mixtures or the corresponding formulations, are applied by treating the harmful fungi or the plants, seeds, soils, areas, materials or spaces to be kept free from them with a fungicidally active amount of the mixture, or of the compounds I and II, or I and III in the case of separate application. Application can be effected before or after infection by the harmful fungi.

Examples of the synergistic action of the mixtures according to the invention against harmful fungi The fungicidal action of the compounds and of the mixtures was demonstrated by the following experiments:

The active ingredients, separately or together, were prepared as a 10% emulsion in a mixture of 70% by weight of cyclohexanone, 20% by weight of Nekanil® LN (Lutensol® AP6, wetting agents having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

Evaluation was by determining the infected leaf areas in percent. These percentages were converted into efficacies. The expected efficacies of the mixtures of the active ingredients were determined using Colby's formula [R. S. Colby, Weeds 15, 20–22 (1967)] and compared with the observed efficacies. colby's formula:

$$E = x + y - x \cdot y / 100$$

E expected efficacy, expressed in % of the untreated control, when using the mixture of the active ingredients A and B at the concentrations a and b x efficacy, expressed in % of the untreated control, when using active ingredient A at a concentration of a y efficacy, expressed in % of the untreated control, when using active ingredient B at a concentration of b An efficacy of 0 means that the infection level of the treated plants corresponds to that of the untreated control plants; an efficacy of 100 means thats the treated plants were not infected.

Activity against *Botrytis cinerea* (gray mold)

Bellpepper seedings (cultivar: "Neusiedler Ideal Elite") having 4–5 leaves were sprayed to runoff point with the preparation of the active ingredient. After the plants had dried, they were sprayed with a conidia suspension of the fungus *Botrytis cinerea* and kept for 5 days at 22–24° C. and high atmospheric humidity. The test was evaluated visually.

The test results are complied in the tables which follow:

Activity of the active ingredients when applied separately:

| Active ingredient | Rate of application [ppm] | Efficacy [%] |
|---|---|---|
| I.1 (R = H) | 200 | 36 |
|  | 125 | 36 |
|  | 100 | 49 |
|  | 50 | 36 |
| I.2 (R = F) | 200 | 61 |
|  | 125 | 36 |
|  | 100 | 49 |
|  | 50 | 10 |
| II (Captan) | 100 | 0 |
|  | 50 | 23 |
|  | 25 | 0 |
|  | 12.5 | 10 |
| III (Folpet) | 100 | 36 |
|  | 50 | 23 |
|  | 25 | 10 |
|  | 12.5 | 0 |
| untreated control | —/— | 0 |

| Synergistic mixture | | | | |
|---|---|---|---|---|
| Active ingredients | ppm | Ratio | Efficacy observed | calculated |
| I.1 + II | 125 + 12.5 | 10/1 | 87 | 42 |
|  | 200 + 200 | 1/1 | 94 | 50 |
|  | 100 + 100 | 1/1 | 87 | 49 |
|  | 50 + 50 | 1/1 | 81 | 50 |
| I.1 + III | 125 + 12.5 | 10/1 | 87 | 36 |
|  | 200 + 200 | 1/1 | 87 | 50 |
|  | 100 + 100 | 1/1 | 91 | 67 |
|  | 50 + 50 | 1/1 | 87 | 50 |
| I.2 + II | 125 + 12.5 | 10/1 | 87 | 65 |
|  | 200 + 200 | 1/1 | 74 | 50 |
|  | 100 + 100 | 1/1 | 81 | 49 |
|  | 50 + 50 | 1/1 | 81 | 31 |
| I.2 + III | 125 + 12.5 | 10/1 | 74 | 61 |
|  | 200 + 200 | 1/1 | 81 | 50 |
|  | 100 + 100 | 1/1 | 94 | 67 |
|  | 50 + 50 | 1/1 | 96 | 31 |

We claim:

1. A fungicidal composition comprising
a) an oxime ether carboxamide compound of the formula I

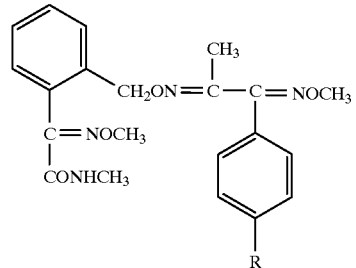

where R is hydrogen or halogen, and b) a phthalimide selected from the group consisting of the compounds II and III

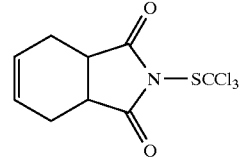

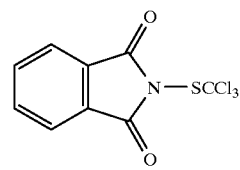

in a synergistically active amount.

2. The fungicidal composition defined in claim 1, comprising the phthalimide compound II.

3. The fungicidal composition defined in claim 1, comprising the phthalimide compound III.

4. The fungicidal composition defined in claim 1, wherein the weight ratio of the compound of the formula I to the compound II or the compound III is 1:1 to 1:100.

5. A method of controlling harmful fungi, which comprises treating the harmful fungi, their environment, or the plants, seeds, soils, areas, materials or spaces to be kept free from said fungi with a synergistically effective amount of the compound of the formula I as defined in claim 1 and the compound II as defined in claim 1 or the compound III as defined in claim 1.

6. The method defined in claim 5, wherein the compound of the formula I and the compound II or the compound III are applied simultaneously together or separately, or in succession.

7. The method defined in claim 5, wherein from 0.005 to 0.5 kg/ha of the compound of the formula I are applied.

8. The method defined in claim 5, wherein from 0.1 to 5 kg/ha of the compound II or the compound III are applied.

* * * * *